United States Patent [19]
Obuchi et al.

[11] Patent Number: 5,505,843
[45] Date of Patent: Apr. 9, 1996

[54] SYSTEM FOR CONTROLLING WATER TREATMENT BASED ON PLANKTON MONITORING

[75] Inventors: Misako Obuchi; Shoji Watanabe, both of Hitachi; Mikio Yoda, Tokai; Naoki Hara, Hitachi; Bunchi Kimura, Ueda; Hayao Yahagi, Hitachi, all of Japan

[73] Assignee: Hitachi, Ltd., Tokyo, Japan

[21] Appl. No.: 267,024

[22] Filed: Jun. 21, 1994

[30] Foreign Application Priority Data

Jul. 6, 1993 [JP] Japan .................................. 5-166782

[51] Int. Cl.⁶ .................................................. B01D 17/12
[52] U.S. Cl. ........................... 210/94; 210/85; 210/96.1; 210/143; 210/259; 210/411; 422/62
[58] Field of Search ...................................... 435/29, 32, 3, 435/34, 39; 422/62; 436/39, 55; 210/85, 87, 96.1, 143, 259, 411, 192, 739, 748, 806, 764, 614, 94, 602

[56] References Cited

U.S. PATENT DOCUMENTS 5,160,604 11/1992 Nakamura et al. ..................... 210/85
5,225,333 7/1993 Krause et al. ............................ 435/29
5,324,431 6/1994 Watanabe et al. ...................... 210/614

FOREIGN PATENT DOCUMENTS 4-83575   3/1992 Japan ....................................... 210/85
92/01869 10/1992 WIPO ...................................... 435/29

OTHER PUBLICATIONS

"Instrumentation and Automation Systems for Waterworks", Kawabe et al, Published in Toshiba Review—No. 133 (May–Jun. 1981).

Primary Examiner—Joseph W. Drodge
Attorney, Agent, or Firm—Antonelli, Terry, Stout & Kraus

[57] ABSTRACT

In a water supply plant which cleans water taken in from such sources of intake water as lakes and marshes, dams, rivers and so on and delivers the water as city water, obstructions to water treatment is predicted and methods for preventing the obstruction are decided, by measuring kinds and quantity of plankton and comparing the measured data with rules representing relations among kinds and quality of plankton, obstructions to water treatment and counteractions to such obstructions stored in a rule base in advance.

10 Claims, 4 Drawing Sheets

SYSTEM FOR CONTROLLING WATER TREATMENT BASED ON PLANKTON MONITORING

BACKGROUND OF THE INVENTION

1. Field of the Invention

The present invention relates to a system for supporting operations of a water which is supply plant to clean water taken in from such sources of intake water as lakes and marshes, dams or rivers which is delivered as city water.

2. Description of the Related Art

Generally, in a water supply plant, substance harmful to a human body is pasteurized by adding chemicals having sterilizing effect into water taken in from lakes and marshes, dams or rivers and substance suspending in water is agglutinated and precipitated by adding chemicals having agglutinating effect into the water, and the processed water is further filtered and delivered as city water.

However, in such closed water area as lakes and marshes, dams and so on, phytoplankton sometimes breed abnormally, which causes filtration blockade, obstruction to agglutination or turbidity increase. Offensive smell such as mold smell felt when drinking city water is often caused by plankton.

As a conventional art of a system for supporting operations of a water supply plant, a technique monitoring water quality of such sources of intake water as lakes and marshes, dams, rivers etc., sending water quality data to the water supply plant and making use of the data for controlling water intake is described in Japanese Patent Application Laid-Open No.35165/1991. However, the water quality monitoring confirms only presence of toxic substance by monitoring behaviors of fishes. A technique for supporting process in a water supply plant by monitoring kinds and quantity of plankton in the source of intake water has not been reported yet. As another conventional art, a turbidity meter calculating the density of plankton is presented in Japanese Patent Application Laid-Open No.71339/1986, which is devised on the basis of the fact that the turbidity of water in rivers or lakes and marshes is caused by mixing of earth and sand or by generation of plankton, and is not aimed to be applied to water treatment. And, a method for detecting density of plankton in water by quantity, color and smell of forms in the sampled and formed water containing plankton is devised in order to find generation and coming nearer of plankton and take counteractions to it as soon as possible for preventing damage to fish cultivation by red tide, in Japanese Patent Application Laid-Open No.155851/1981, which is not aimed to be applied to water treatment. Furthermore, a water quantity monitoring system for managing water quality of a water tank used to cultivation of plankton for feeding fishes and shellfishes is devised in Japanese Patent Application Laid-Open No.108664/1991, which is not also not aimed to support water treatment.

SUMMARY OF THE INVENTION

Objects of the Invention

An object of the present invention is to present a system for supporting operations of a water supply plant to prevent objections to water treatment due to plankton by monitoring plankton contained in sources of intake water and reflecting the monitoring information to water treatment in a water supply plant which cleans water taken in from such sources of intake water as lakes and marshes, dams, rivers and so on and delivers the water as city water.

Another object of the present invention is to offer a system for supporting operations of a water supply plant to control the conditions of ozone injection processing by monitoring plankton contained in sources of intake water in a water supply plant which operates a function of oxidizing decomposition of substance generating offensive smell by injecting ozone into the water in the process for cleaning water taken in from such sources of intake water as lakes and marshes, dams, rivers and so on.

Statement of the Invention

One of features of the present invention is to present guidance of cleaning water methods in a water supply plant by measuring kinds and quantity of phytoplankton in sources of intake water such as lakes and marshes, dams, rivers, etc. and comparing the measured data with rules representing relations among kinds and quantity of plankton, obstructions to water treatment and counteractions which are prepared in advance. A system for supporting operations of a water supply plant to realize the above-mentioned feature has a computer system comprising a plankton measuring apparatus for measuring kinds and quantity of plankton and a rule base for storing the rules representing relations among kinds and quantity of plankton, obstructions to water treatment and counteractions to the obstructions. The computer system further comprises a information processing circuit for deciding cleaning water methods by taking in and comparing the data measured by the plankton measuring apparatus with the rules representing relations among kinds and quantity of plankton, obstructions to water treatment and counteractions, a data base for storing the data measured by the plankton measuring apparatus and the decided cleaning water methods, and an output means for outputting the guidance of cleaning water methods. Any means capable of outputting contents of the guidance are applicable as the output means and a phonetic means informing the contents of guidance besides a means presenting character display can be also applied. A means printing out the contents of guidance may be preferably provided.

By the present invention, it is possible to predict the obstructions to water treatment by detecting kinds and quantity of plankton living in sources of intake water based on the knowledge that the relations among kinds and quantity of plankton, obstructions to water treatment and counteractions to the obstructions can be represented as rules. And, a system for supporting operations of a water supply plant predicting obstructions to water treatment caused by plankton and presenting counteractions to prevent the obstructions is devised by the present invention. The system has a rule base built on the basis of the above-mentioned knowledge.

Consequently, by the present invention, an operator without much experiences on water treatment is capable of providing counteractions to prevent the obstructions caused by plankton, which has the effect of removing offensive smell felt when drinking the water.

DETAILED DESCRIPTION OF THE EMBODIMENTS

Hereinafter, details of the present invention are explained based on embodiments referring to drawings. However, the present invention is not restricted to the explained embodiments.

Figure 1:
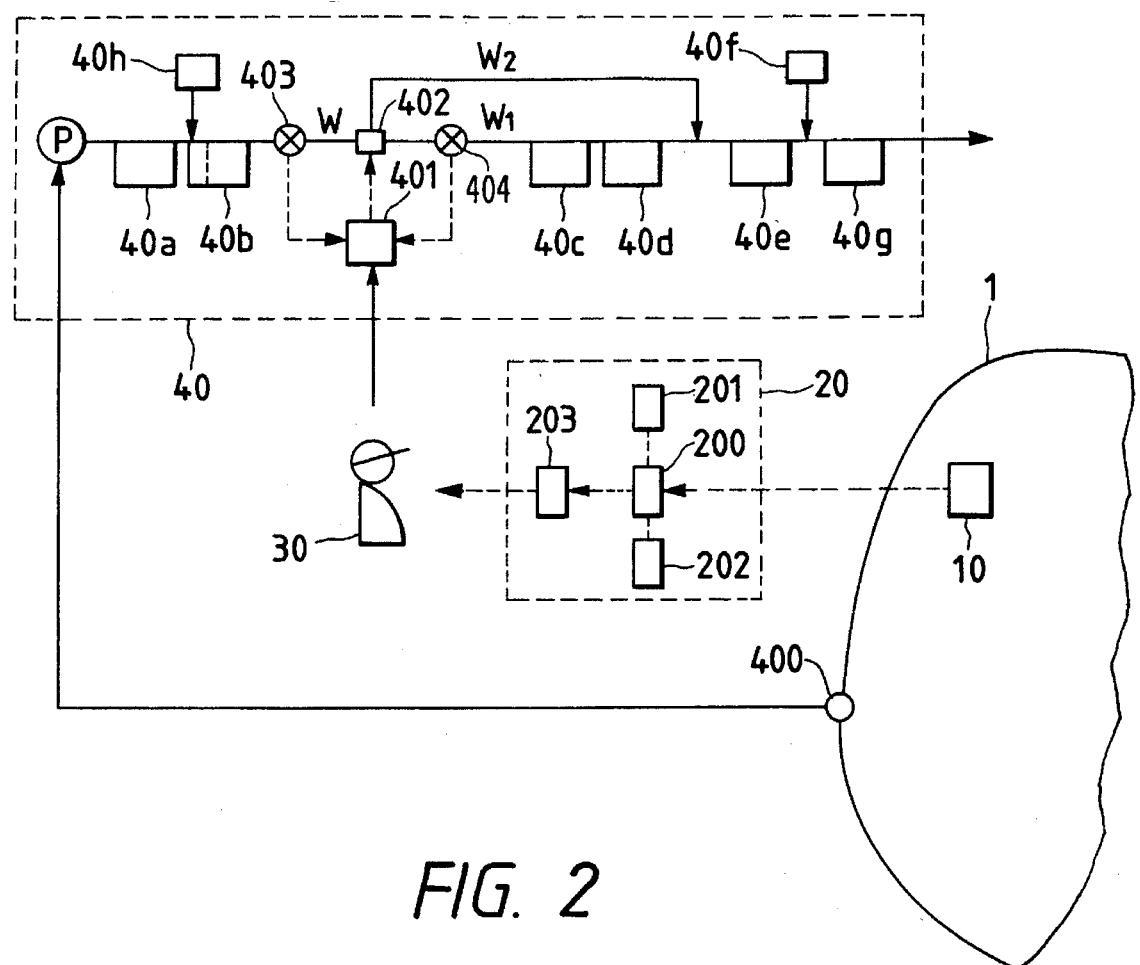
FIG. 1 is a flow diagram showing the outline of a system for supporting operations of a water supply plant by the present invention.

FIG. 1 is a flow diagram showing the outline of a system for supporting operations of a water supply plant by the present invention. Kinds and quantity of plankton are measured by a plankton measuring apparatus 10 at an optional place of such a source of intake water 1 as a lake, a marsh, a dam and so on. The constitution of the plankton measuring apparatus 10 is described in detail later. It is preferable to provide the plankton measuring apparatus 10 near an water intake 400 and the number of the measuring apparatus 10 is not fixed to one. The data measured by the plankton measuring apparatus 10 are input to a computer system 20. The computer system 20 has an information processing circuit 200, a data base 201, a rule base 202 and a displaying means 203, and decides an optimal cleaning water method on the basis of the information gained by the plankton measuring apparatus 10 on the plankton living in the source of intake water 1. An operator confirms the decision of the computer system 20 and sends necessary commands to a water supply plant 40.

Figure 2:
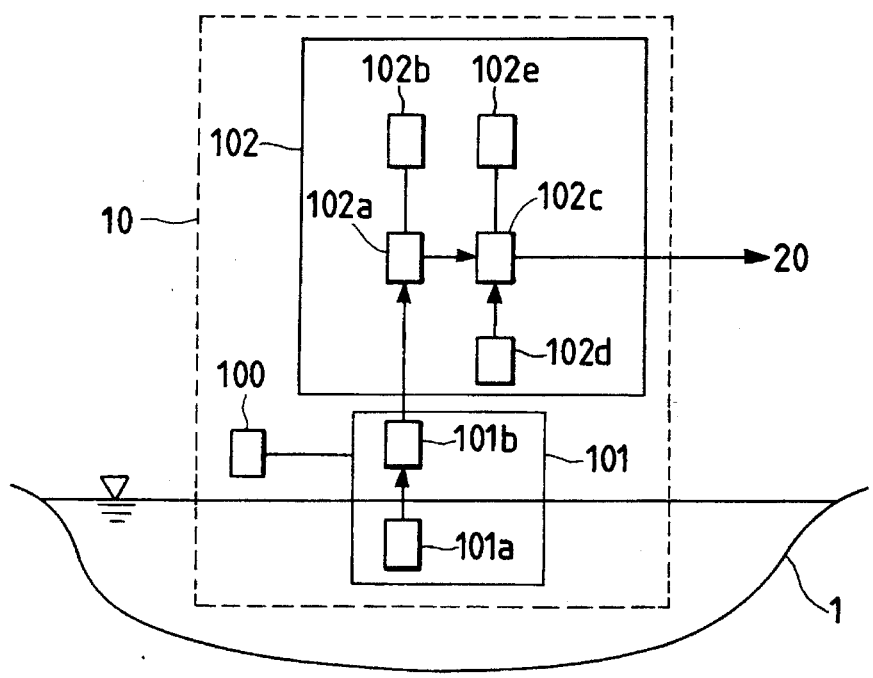
FIG. 2 is a block diagram showing the detailed constitution of a plankton measuring apparatus.

The water supply plant 40 includes such ordinary agglutination and sedimentation processing installations as a pump P for taking in raw water from the water intake 400 of the source of intake water 1, a raw water storage well 40a, a sedimentation basin 40b, a chlorine injection apparatus 40f, a water delivering basin 40g, etc., further, a high power water treatment installation including an ozone contact basin 40c and a biological active carbon contact basin 40d. The high power water treatment installation themselves is conventional. In the embodiment, a water distribution apparatus 402 is provided between the sedimentation basin 40b and the ozone contact basin 40c via valves 403 and 404 and a control apparatus 401 is provided at the water distributing apparatus 402. Operations of each apparatus or system are explained hereinafter. The plankton measuring apparatus 10 measures the generating number of each kind of plankton and sends the measured data to the computer system 20. The computer system 20 decides an optimal cleaning water method and presents guidance according to the decision on the basis of the later-mentioned rules of relations among kinds and quantity of plankton, water quality and counteractions stored in the rule base of the computer system 20. The operator 30 operates and manages the water supply plant 40 based on the guidance by the computer system 20. As an example of a plankton measuring apparatus 10, the detailed constitution of an apparatus for online measuring kinds and quantity of plankton by image processing is shown in FIG. 2. The plankton measuring apparatus 10 comprises a control part 100, a picture pickup part 101 and a image processing part 102. The control part 100 starts the picture pickup part 101 at the predetermined interval. The picture pickup part 101 receives the starting signal from the control part 100 and picks up an enlarged grey image of the raw water sampled in the source of intake water by a picture pickup device 101a. The picture pickup device 101a has a function of converting the grey image into digital code signals by use of an A/D converter. As a picture pickup device, a television camera is very adequate. In Japanese Patent Application Laid-Open No.40340/1992, a picture pickup device adequate to pickup of microscopic articles in liquid is described, and such a picture pickup device is also applicable in the present invention. The grey image picked up by the picture pickup device 101a is converted into digital code signals by the A/D converter 101b and sent to a image processing circuit 102a of the image processing part 102.

The image processing circuit 102a recognizes articles by processing the received picture and calculates such feature parameters as an area, a shape factor, etc. to each recognized article. The above-mentioned articles are plankton or refuse. And, in the image processing, a binary coding processing for recognizing plankton with the predetermined threshold level of brightness, a noise removal processing, a labelling processing and so on are used.

Figure 5:
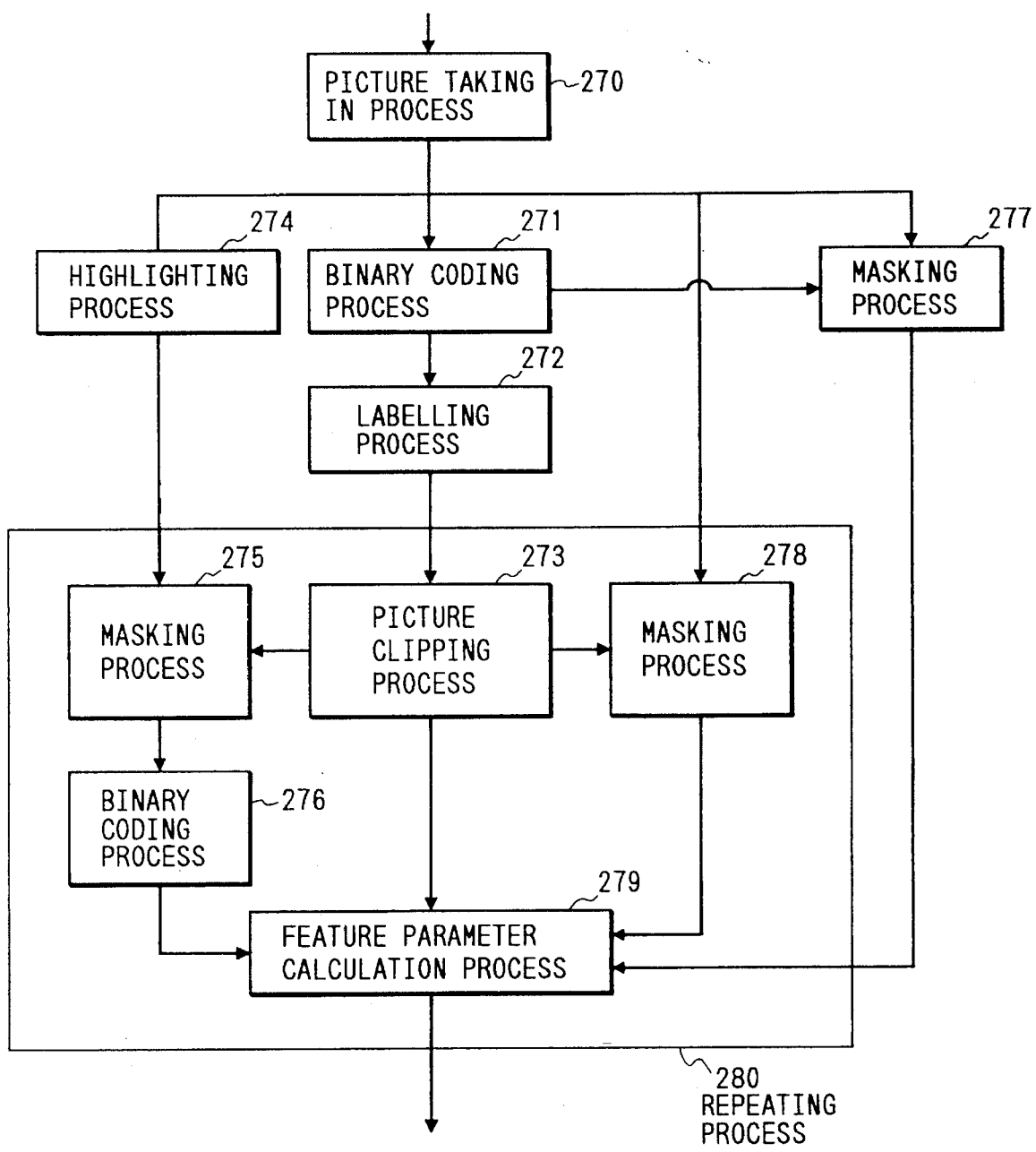
FIG. 5 is a flow chart showing procedures of image processing in a plankton measuring function.

A process flow example of the image processing circuit 102a is explained by using FIG. 5. The grey image picked up by the picture pickup device 101a and converted into binary code signals are firstly memorized in a grey image memory (not shown by a figure ) as a original picture in the step 270 of the picture taking in process. To the original picture shown in the stage (a) of FIG. 6, various kinds of picture information on all suspending articles of the original picture are obtained in the steps of binary coding process 271, labelling process 272 for labelling the articles recognized on the binary coded picture shown in the stage (c) of FIG. 6, picture clipping process 273 for clipping pictures of the labelled plural articles one by one, highlighting process 274 for selectively highlighting the brightness of the original picture, the first masking process 275 for masking the highlighted picture shown in the stage (b) of FIG. 6 with the binary coded picture clipped in the picture clipping process 273, binary coding process 276 for binary coding the highlighted picture masked in the first masking process 275, the second masking process 277 for masking the original picture with the binary coded picture obtained in the binary coding process 271, the third masking process 278 for masking the original picture with the binary coded picture obtained in the picture clipping process 273 and feature parameter calculation process 279 for calculating feature parameters of each article by using the input binary coded and grey images. And, in the step of repeating process 280, feature parameters of all articles are calculated in order by clipping pictures of articles one by one. The grey image taken in at the step 270 of picture taking in process as the original picture has the brightness information $G(i,j)$, for example, graded into 256 gradations corresponding to brightness of pixels which is input into the binary coding process 271, the highlighting process 274, the second masking process 277 and the third masking process 279. In the binary coding process 271, an optional threshold level of brightness is predetermined and a article ("1" code) and liquid phase ("0" code) are separated and recognized by binary coding the picture using the following equation.

$$\text{If } G(i,j)<L, \text{ then } B(i,j)=1, \tag{1}$$

If $G(i,j) > L$, then $B(i,j) = 0$, where

G(i,j): a brightness function of a pixel (X coordinate, Y coordinate) in the grey image= brightness value of the pixel, B(i,j): a binary function of a pixel (X coordinate, Y coordinate) in the grey image= binary coded brightness value of the pixel, L: threshold level of brightness.

The labelling process 272 executes a function of obtaining a contour of a article in the binary coded picture gained in the binary coding process 271 and recognizing a article having a closed contour, and a function of attaching such recognition codes as the ordering number, a notation, a name, etc. to each recognized article. The picture clipping process 273 executes a function of outputting the binary coded picture labelled in the labelling process 272 in order. The binary coded picture is output to the first masking process 275, the third masking process 278 and the feature parameter calculation process 279 by each picture of article pictures, and the next one is clipped and output after the feature parameter calculation of the previous one is finished. The picture clipping processing is repeated until the feature parameter calculation is completed for all recognized articles.

The highlighting process 274 selectively highlights the brightness of the original picture G(i,j) input in the picture taking in process 270. Laplacian processing is used in the highlighting process 274. In the Laplacian processing, the brightness difference between two pixels neighboring each other is strengthened. The Laplacian processing is explained by using an example of 8 direction Laplacian processing. On having an eye to optional nine pixels neighboring each other and defining the brightness of the central pixel as D and those of the surrounding ones as $D_1$–$D_8$, the 8 direction Laplacian processing is expressed by the following equation.

$$D' = 8D - \Sigma D_i, \qquad (2)$$

where D': the brightness of the central pixel after processing.

Figure 6:
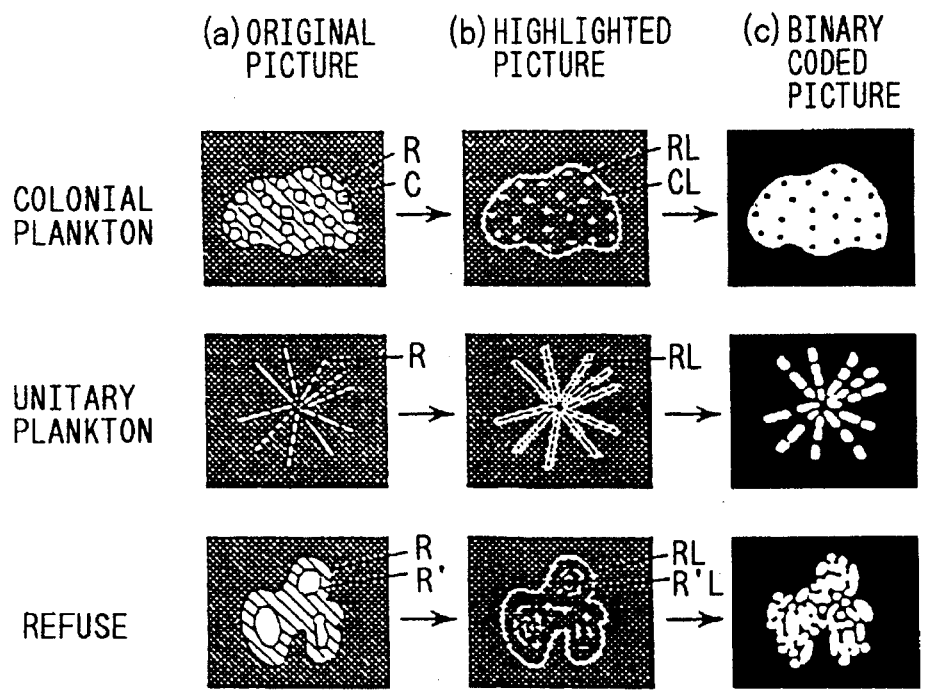
FIG. 6 shows changes of processed pictures in image processing.

The calculation of brightness correction is executed to all pixels of the grey image, and the highlighted picture having the new brightness information is obtained as shown in the stage (b) of FIG. 6 where the highlighted pictures obtained by the Laplacian processing to the original pictures of colonial plankton, unitary plankton and refuse are shown as examples. The highlighted picture obtained by the Laplacian processing is a picture having the highlighted regions where changes of the brightness in the original picture are larger than other regions. For example, a contour part of an article or a brightness changing part in an article is highlighted. The contour part of an article R or the brightness changing part in an article R' is highlighted by the Laplacian processing and pictured as RL and R'L as shown in the stage (b) of FIG. 6. In the colonial plankton in which the same kind of cells aggregate densely, the central part C of each cell having the large brightness change is highlighted and pictured as CL also as shown in the stage (b) of FIG. 6. In the highlighting process 274, the regions having not uniform brightness are selectively highlighted as mentioned above.

The first masking process 275 masks the grey image obtained in the highlighting process 274 with the binary coded picture from the picture clipping process 273. By the masking processing, only the regions of the highlighted picture corresponding to the regions having the brightness information "1" of the binary coded picture are selectively extracted. And, the regions on the grey image are masked by using the addresses of the regions corresponding to the addresses which are supplemented to the regions on the clipped binary coded picture. By the masking process, the grey image masking each of the article images can be obtained.

The binary coding process 276 processes the grey image masked in the first masking process 275 by the binary coding way and recognizes every article. In the stage (c) of FIG. 6, the binary coded pictures are shown, which are the results of masking the grey images in the stage (b) of the figure. The colonial plankton are recognized as a large lump, which is because the colonial plankton have a more uniform brightness internally than the unitary plankton or the refuse and a smaller part highlighted by the Laplacian processing. On the other hand, the refuse is recognized as a dispersing shape due to the jagged contour of the refuse. The feature parameters of the binary coded picture obtained in the binary coding process 276 are calculated in the feature parameter calculation process 279.

The second masking process 277 masks the original picture G(i,j) input from the picture taking in process 270 with the binary coded picture obtained in the binary coding process 271. In the masking process 277, the bit data of the binary coded picture are inverted, that is, the liquid phase bit data "0" are inverted to "1", then, only the liquid phase region of the grey image are selectively extracted. The binary coded picture obtained in the binary coding process 271 is a picture for recognizing all suspending articles in the original picture G(i,j) with which a liquid phase picture can be obtained by inverting the bit data of the binary coded picture obtained in the binary coding process 271 and using the inverted bit binary coded picture for masking the grey image. The data of the masked picture obtained in the second masking process 275 are used to calculate feature parameters of the liquid phase picture of the original picture.

The third masking process 278 masks the original picture G(i,j) input from the picture taking in process 270 with the binary coded picture sent from the picture clipping process 273. By the third masking processing, only the region of the grey image corresponding to the regions of article images clipped with the binary coded picture are selectively extracted. The data of the masked picture obtained in the third masking process 278 are used to calculate feature parameters of each clipped article image.

Figure 7:
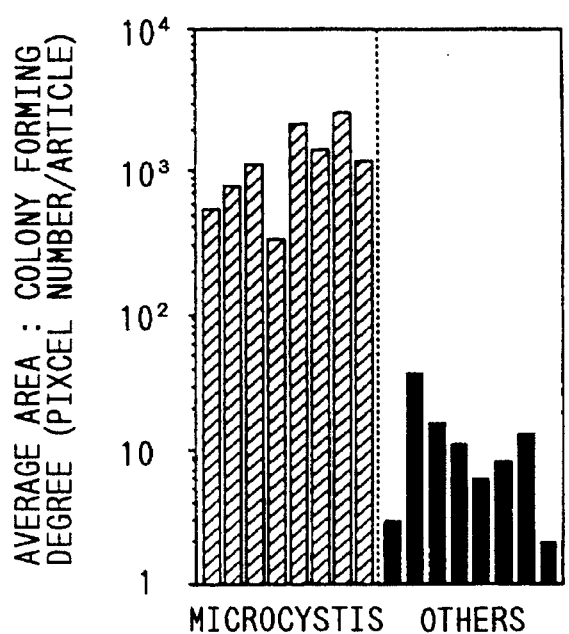
FIG. 7 is a graph comparing a feature parameter of plankton with that of others based on the results of image processing.

The feature parameter calculation 279 calculates feature parameters of each article image and the liquid phase image by using the binary coded picture from the binary coding process 276 and the picture clipping process 273, and the grey image from the second masking process 277 and the third masking process 278. Firstly, the number of articles, an area of each article, the total area of all articles, an area distribution, etc. are calculated by using the binary coded picture from the binary coding process 276. Then, the colony forming degree representing uniformity of brightness in an article is obtained by using the calculation results. As the colony forming degree, for examples, the ratio of the total area of all articles to the number of articles (the average area), the ratio of the maximum area of individual article area to the total area of all articles (the maximum area ratio), the standard deviation of article areas, and so on can be used. In FIG. 7, on taking up the average area as the colony forming degree, the average areas of colonial plankton lumps (water bloom) obtained by image processing are shown in comparison with those of unitary plankton and refuse. The average areas of the colonial plankton lumps are largely different from those of other articles, which indicates that the parameter of average area can reflect the colony forming degree.

The below-mentioned feature parameters are calculated by using the binary coded picture sent from the picture clipping process 273, that is, the feature parameters: an area, an circumferential length, the number of holes, the ratio of whole hole area to the article area, the ratio of a minor axis to a major axis, a shape factor (representing complexity of a contour shape), a circle shape factor (representing the nearness in shape to a circle), the ratio of the article area to that of a circumscribed rectangle, the shortest distance from the center of gravity to a circumference (the smallest radius)$^2$, the longest distance from the center of gravity to a circumference (the largest radius)$^2$, the average value of distances from the center of gravity to a circumference, the number of X direction changes on tracing the circumference, the number of Y direction changes on tracing the circumference, the number of downward projecting parts, the number of terminal points of line segments, the number of crossing points of line segments and so on of each article (plankton and refuse).

The brightness information is calculated by using the grey image from the second masking processing 277 and the third masking process 278. The maximum, minimum and average brightness of the liquid phase image are calculated in the second masking process 277, and the same parameters of each article image in the third masking process 278.

The picture processed by the image processing circuit 102a shown in FIG. 2 is stored with the enlarged grey image before image processing in the picture memory 102b.

The feature parameters obtained by the image processing circuit 102a are input into the information processing circuit 102c. The information processing circuit 102c judges the kinds of articles on the basis of rules input in advance into the rule base 102d and counts the articles in each kind. For example, a rule for determining the kinds of plankton such as "If the article area is less than the predetermined value $a_1$ and the ratio of the whole hole area to the article area is more than the predetermined value $a_2$, then the article is a plankton A." is input in advance into the rule base 102d. The counting results in the information processing circuit 102c are sent to the computer system 20 and stored in the data base 102e.

Now, it is desirable that the plankton measuring apparatus 10 is started by the predetermined interval and can be also operated on demand based on the judgement of the operator 30 so as to correspond to a water quality accident or abnormal weather. Although the picture pickup part 101 and the image processing part 102 are provided in the plankton measuring apparatus 10 in FIG. 2, the image processing part 102 can be realized also in the computer system 20. To the plankton measuring apparatus 10, an apparatus adopting the image processing technique is applied in the embodiment, and a chlorophyll meter or an plankton measuring method by laser techniques using optical fibers is also applicable. In the embodiment, plankton are in-line measured by the plankton measuring apparatus 10 provided in the source of intake water, and plankton can be also off-line measured by using sampled water.

The raw water taken in from the source of intake water 1 via the water intake 400 is led to the raw water storage well 40a and the sedimentation basin 40b. It is desirable to divide the sedimentation basin into tow rooms of which the front room is used to agglutinate the substance suspending in the water into flocks by injecting chemicals 40h and the behind room to precipitate and remove the flocks and the mixture of sand or soil. The raw water (its flow rate is W) from which sand and soil are removed is branched into two paths by the water distribution apparatus 402 based on the command from the control apparatus 401. That is, a part of the raw water flow is led to the high power water treatment installation having the ozone contact basin 40c and the biological active carbon contact basin 40d (its flow rate is $W_1$); and the rest raw water (its flow rate is $W_2$. $W_2=W-W_1$) is branched to the other path. Coloring and smelling substance is removed from the raw water led to the high power water treatment installation there. The water which passed the high power water treatment installation and the water branched to the other path $W_2$ both are led to the filtration basin 40e. The water from which microscopic suspensions are removed in the filtration basin 40e is led to the water delivering basin 40g after pasteurized by chlorine injected by the chlorine injection apparatus 40f.

Now, if the quality of the raw water is good, then the high power water treatment is not necessary. Therefore, $W_1=0$, that is, $W=W_2$.

If the smell density of the raw water is high and it can not be dealt with by the usual water treatment, the ratio of the branched water is decided by the later-described equation (4) in accordance with the smell density.

Generally, the nearer the value of $W_1$ is to 0, the more the operation cost of the water supply plant 40 is saved, since operation of the high power water treatment installation comprising the ozone contact basin 40c and the biological active carbon contact basin 40d requires more energy. Then, it is effectual to decide the ratio of branched water ($W_1/W$) based on the water quality information of the source of intake water 1 by the computer system 20.

An example of deciding the ratio of branched water is explained to the case assuming that a plankton A is a plankton forming diosmine which causes mold smell. The generation number of plankton A per unit water quantity is sent from the plankton measuring apparatus 10 to the information processing circuit 200 of the computer system 20 and stored in the data base 201. The information processing circuit 200 calculates the concentration of diosmine $G_0$ in the raw water by using the rules in the rule base 202, for example, as follows.

$$G_0 = \alpha B \qquad (3)$$

,where

α: diosmine forming coefficient of plankton A

B: density of plankton A in raw water (cells/ml).

Since the following relation holds if the target concentration of diosmine in the delivered water is G, $$G_0 : G = W : W_2 \qquad (3)$$

Then, the ratio of the water to be processed in the high power water treatment ($W_1/W$) is expressed by the following equation from Eq.(4).

$$W_1/W = (G_0 - G)/G_0 \qquad (5)$$

The relations between the kind and quantity of plankton and the formed substance as described by Eqs (4)–(5) are all input in the rule base 202 in advance. For example, the relations between the smelling substance dimethylisoborneol causing also mold smell and blue-green algae such as Phormidium, Oscillatoria, etc. are input as rules.

The support contents for the water treatment as explained above are decided by the information processing circuit 200 and output as operation guidance on the display means 203 such as a monitor. The operation guidance are not restricted to those for removing the smelling substance and it is also possible, for example, to present the operation guidance for preventing the obstructions to water treatment such as the filtering blockade. That is, Synedra Ehrenberg and Nitzschia Hassall are representative plankton causing the filtering blockade in the water supply plant, and the operation guidance such as backwash interval reducing of the filtering basin 40e, is presented if the density of those plankton exceeds the predetermined level.

An operator 30 manages the processing in the water supply plant 40 on the basis of the presented operation guidance by the computer system 20. Concretely mentioning, the operator 30 adjusts the ratio of the water processed in the high power water treatment installation ($W_1/W$) by operating the water distribution apparatus 402 via the control apparatus 401. And, it is effective on improving the efficiency of operations of the operator 30 that a display apparatus (not shown in a figure) for displaying the quantity of raw water (W) and the quantity of the water to be processed in the high power water treatment ($W_1$) is provided at the control apparatus 401. The control apparatus 401 can automatically adjust the water distribution apparatus 402 in accordance with the ratio ($W_1/W$) set by the operator 30. And, it is also possible that the setting of the ratio ($W_1/W$) is automatically done by the computer system 20 without operations by the operator 30. That is, the water distribution apparatus 402 is automatically controlled by the control apparatus 401 of the water supply plant 40 directly receiving the information for supporting the water treatment decided by the information processing circuit 200 of the computer system 20. By appropriately executing the automatic controlling, an operator has not to always stay at the water supply plant 40 and the labor of an operator can be considerably saved.

Figure 3:
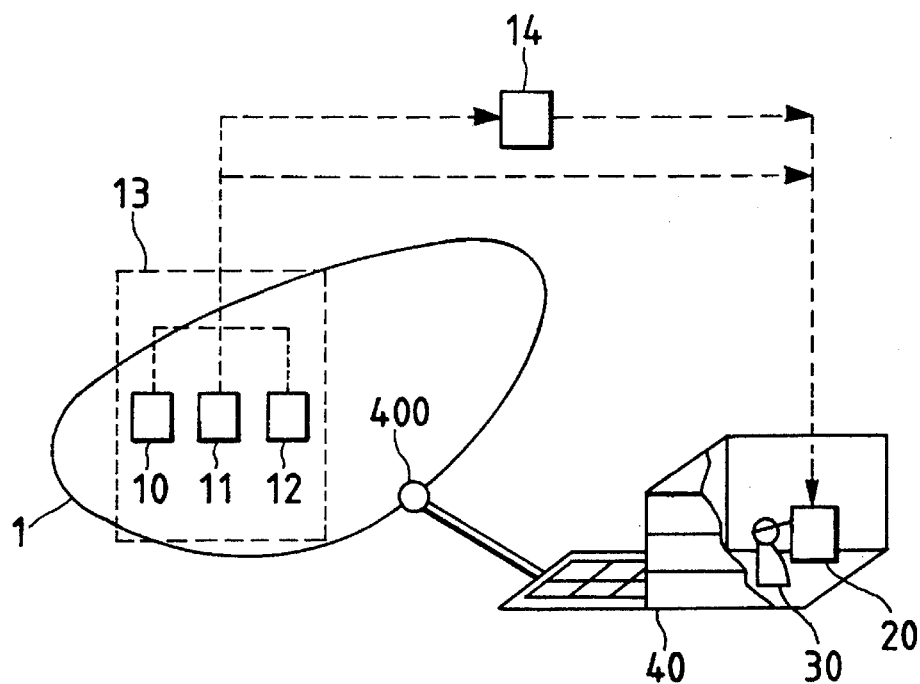
FIG. 3 is a block diagram showing an embodiment of the system for supporting operations of a water supply plant and a water supply plant supported thereby.

Although the information used to the support of water treatment is the information only on plankton in the source of intake water 1 in the embodiment explained above, it become possible to more subtly support the water treatment if information on the water quality such as water temperature, turbidity, etc. is supplementarily utilized. And, it is also effectual to make use of the information on causative substance of water pollution such as smelling substance inferred from the information on plankton and the water quality in the source of intake water 1. Another embodiment having the above-mentioned supplementary function is shown in FIG. 3.

In the another embodiment, a water quality measuring apparatus 11 and a poison monitoring apparatus 12 besides the plankton measuring apparatus 10 are provided in the source of intake water 1, in addition to the plankton measuring apparatus 10. Then, the plankton measuring apparatus 10, the water quality measuring apparatus 11, the poison monitoring apparatus 12, etc. are generally named as a water quality state monitoring system 13. The information from the water quality state monitoring system 13 is input into a substance determination apparatus 14. And, the results of the substance determination are input into the computer system 20 in the water supply plant 40 which decides an optimal cleaning water method and presents the corresponding operation guidance. An operater 30 manages the water supply plant 40 based on the presented guidance.

In a system for supporting operations of a water supply plant by the another embodiment, the water quality state monitoring system 13 comprising the plankton measuring apparatus 10, the water quality measuring apparatus 11 and the poison monitoring apparatus 12 monitors the states of water quality, a substance determination apparatus 14 determines causative substance of water pollution based on the obtained monitoring information, and the computer system 20 decides an optimal cleaning water method on the basis of the determined substance and presents the corresponding operation guidance. The constitution and operations of each apparatus composing the system for supporting operations of a water supply plant are explained bellow.

The plankton measuring apparatus 10 measures plankton in the source of intake water 1 as explained in the embodiment shown by FIG. 1. The water quality measuring apparatus 11 measures at least one of the measuring items such as pH (degree of acidity), water temperature, water turbidity, smell, DO (dissolved oxygen), BOD (biological oxygen demand), COD (chemical oxygen demand), chlorophyll, and so on, and transmits the measured data by the predetermined interval or continuously to the substance determination apparatus 14 and the computer system 20. And, the poison monitoring apparatus 12 detects anomaly of the raw water, for example, by monitoring behaviors of fishes picked up into pictures and sends alarms to the substance determination apparatus 14 and the computer system 20 when detecting anomaly of water quality, particularly, poison mixing in the raw water.

As mentioned above, the substance determination apparatus 14 and the computer system 20 receive the information on water quality from the three apparatuses of the plankton measuring apparatus 10, the water quality measuring apparatus 11 and the poison monitoring apparatus 12. The substance determination apparatus 14 stores the received information on water quality in a memory and determines the water polluting substance such as smelling substance, toxic substance, etc. in the source of intake water 1 based on the stored information. By the embodiment, it is possible to take counteractions to offensive smell or taste by using the plankton information from the plankton measuring apparatus 10 and the information from a smell sensor of the water quality measuring apparatus 11 together. The substance determination apparatus 14 has a rule base in which the relations between causative substance of water pollution and water quality on which the information are monitored and sent from the above-mentioned three apparatuses. That is, for example, such rules as "If the number of plankton y is more than the predetermined value $y_1$ and the water temperature is more than $y_2$ °C. and the turbidity is more than the predetermined value $y_3$, the causative substance of water pollution is the smelling substance S." are input into the rule base in advance. Such plankton as Synedra Ehrenberg, Nitzschia Hassall and so on causing filtration blockade themselves are the causative substance of water pollution.

The computer system 20 decides an optimal cleaning water method and present the corresponding operation guidance by using the information of water quality from the three apparatuses of the plankton measuring apparatus 10, the water quality measuring apparatus 11 and the poison monitoring apparatus 12 and the information determined by the substance determination apparatus 14. For example, the guidance of stopping the water intake is presented when the poison mixing in the source of intake water 1 is detected. And, it becomes possible to more subtly present guidance corresponding to the smelling substance of diosmine explained in the embodiment shown by FIG. 1. That is, for example, it is possible to avoid such an unrealistic decision as "Mold smell will occur" in the winter, by giving the diosmine forming coefficient α of plankton A of Eq.(2) as a function of water temperature, pH and turbidity, namely, α=f(water temperature, pH, turbidity). Now, main instances of the relations among obstruction to water treatment, its causative plankton and counteractions to it (guidance) are summarized in Table 1(1)–1(3).

Figure 4:
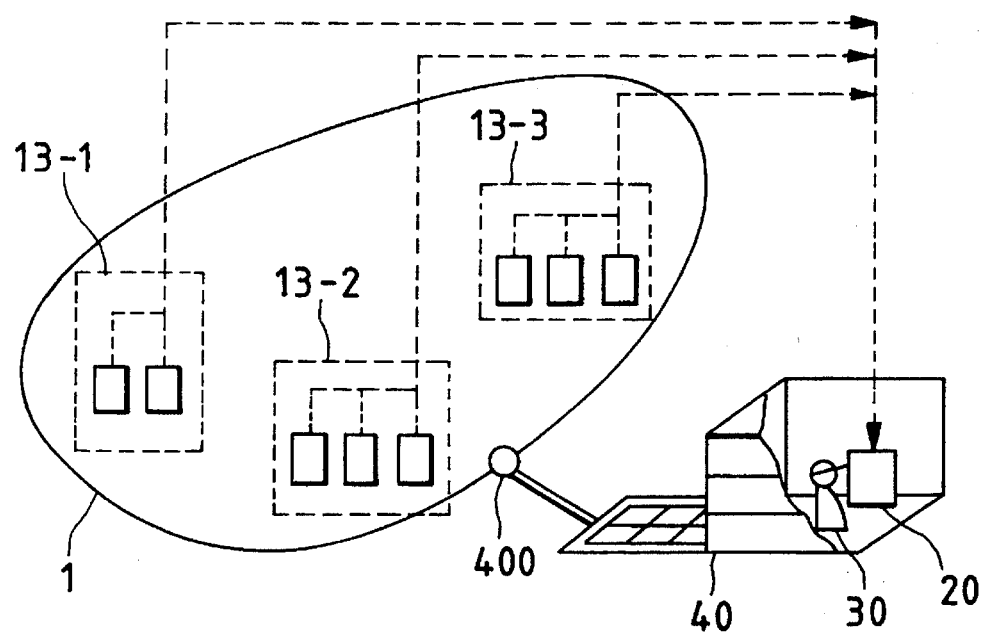
FIG. 4 is a block diagram showing another embodiment of the system for supporting operations of a water supply plant and a water supply plant supported thereby.

Although one water quality state monitoring system 13 comprising the plankton measuring apparatus 10, the water quality measuring apparatus 11 and the poison monitoring apparatus 12 is provided in the embodiment shown by FIG. 3, it is needless to say that a plurality of water quality monitoring systems 13-1, 13-2, 13-3, . . . are effectively provided as shown in FIG. 4. For example, the information from plural water quality monitoring systems is effectively utilized for the water treatment since it is obvious that the monitored water quality states affects the water quality at the neighborhood of the water intake 400 some time behind if the water quality is monitored at the upstream points or the windward points. The elements composing the water quality monitoring system 13 are suitably changed in accordance with the configuration conditions of the ground. That is, the plankton measuring apparatus 10 is indispensable at the region where the red tide is apt to generate because the stream is slow and stagnant but not always necessary at the region where the stream is fast and it is far from the water intake 400. And, the poison monitoring apparatus 13 is very effective if it is provided at the neighborhood of the scupper of a chemical plant, on the other hand, the provision of the poison monitoring apparatus 13 may be not necessary in the region near to a forest, the precipice, the shore of lake and so on where there is scarcely the possibility of poison mixing.

By the present invention as shown in the above-explained embodiment, it is possible to subtly present guidance for the water treatment based on the detailed information such as the generation number of each kind of plankton which is not considered in a conventional system, which further make the quantitative and economical operation management of a water supply plant. That is, it becomes possible to predict obstructions such as the filtering blockade or the mold smell occurrence caused by plankton, etc., decide counteractions to the predicted obstructions and present an operator the corresponding operation guidance.

TABLE 1-(1)

MAIN COUNTERACTIONS TO OBSTRUCTIONS CAUSED BY CAUSATIVE PLANKTON

| Causative plankton | Causative substance of water pollution | Obstruction to cleaning water processing | Counteractions (guidance) |
|---|---|---|---|
| Diatom: Synedra sp. | Plankton itself | Filtration blockade | Interval reduction of filtration basin backwash |
|  |  | Soil smell | Increasing ratio of water for high power water treatment |
| Nitzschia sp. | Plankton itself | Filtration blockade | Interval reduction of filtration basin backwash |
| Fragilaria sp. | Plankton itself | Filtration blockade | Interval reduction of filtration basin backwash |
| Asterionella sp. | Plankton itself | Filtration blockade | Interval reduction of filtration basin backwash |
|  |  | Fishy smell | Increasing ratio of water for high power water treatment |

TABLE 1-(2)

MAIN COUNTERACTIONS TO OBSTRUCTIONS CAUSED BY CAUSATIVE PLANKTON

| Causative plankton | Causative substance of water pollution | Obstruction to cleaning water processing | Counteractions (guidance) |
|---|---|---|---|
| Blue-green algae: Phormidium sp. | 2-MIB, diosmine | Mold smell | Increasing ratio of water for high power water treatment |
| Anabena sp. | Diosmine | Mold smell | Increasing ratio of water for high power water treatment |
| | Plankton itself | Leakage to clean water | Interval reduction of filtration basin backwash Strengthening disinfection (chlorine) |
| | Plankton itself | Filtration blockade | Interval reduction to filtration basin backwash |
| | | Obstruction to agglutination | Increasing addition of agglutination chemicals |
| Oscillatoria sp. | 2-MIB, diosmine | Mold smell | Increasing ratio of water for high power water treatment |
| Lyngbya sp. | Diosmine | Mold smell | Increasing ratio of water for high power water treatment |

TABLE 1-(3)

MAIN COUNTERACTIONS OF OBSTRUCTIONS CAUSED BY CAUSATIVE PLANKTON

| Causative plankton | Causative substance of water pollution | Obstruction to cleaning water processing | Counteractions (guidance) |
|---|---|---|---|
| Microcystis sp. | Microcytine (poison) | Poison mixing | Restriction or stop of water intake |
| | Plankton itself | Leakage to clean water | Interval reduction of filtration basin backwash Strengthening disinfection (chlorine) |
| | | Obstruction to agglutination | Increasing addition of agglutination chemicals |
| Actinomycetes: Streptmyces sp. | 2-MIB, diosmine | Mold smell | Increasing ratio of water for high power water treatment |
| Chlorophyta: Dictyosphacrium sp. | Plankton itself | Leakage to clean water | Interval reduction of filtration basin backwash Strengthening disinfection (chlorine) |
| | | Obstruction to agglutination | Increasing addition of agglutination chemicals |

What is claimed is:

1. A system for supporting operations of a water supply plant, comprising:

plankton measuring means for detecting different kinds of plankton living in a source of intake water and measuring the quantity of each detected kind of plankton;

obstruction predicting means for predicting obstructions to water treatment on the basis of the quantities of the different kinds of plankton measured by said plankton measuring means; and processing method determining means for determining a water treatment method on the basis of obstructions predicted by said obstruction predicting means.

2. A system for supporting operations of a water supply plant according to claim 1, further comprising polluting substance determining means for determining kinds and quantities of substances polluting the water quality on the basis of the quantities of the different kinds of plankton measured by said plankton measuring means, and wherein said processing method determining means is coupled to receive information obtained by said polluting substance determining means.

3. A system for supporting operations of a water supply plant according to claim 2, further comprising:

water quality predicting means for predicting water quality near the source of intake water a predetermined time after measuring parameters of water at the source of intake water using at least two of said plankton measuring means, polluting substance determining means, and a poison monitoring means for detecting poison in the water.

4. A system for supporting operations of a water supply plant according to claim 1, wherein the water supply plant includes at least two different water treatment systems, and further comprising control means for controlling the ratio of raw water distributed to the respective water treatment systems.

5. A system for supporting operations of a water supply plant according to claim 4, wherein one of the different water treatment systems is a high power water treatment system having an ozone contact basin and a biological active carbon contact basin.

6. A system for supporting operations of a water supply plant according to claim 5, wherein the water supply plant has a sedimentation basin, a filtration basin, a chlorine injection installation, and a bypass line for directly sending water which has passed the sedimentation basin to the filtration basin by bypassing the high power water treatment system, said system further comprising:

flow rate determining means for determining a ratio of raw water to be branched to the high power water treatment system on the basis of the data concerning different kinds and quantities of plankton and a flow rate of raw water to be processed; and display means for displaying the determined ratio.

7. A system for supporting operations of a water supply plant, comprising:

plankton measuring means for detecting different kinds of plankton living in a source of intake water and measuring the quantity of each detected kind of plankton, a rule base operable for storing rules representing relations among different kinds of plankton, obstructions to water treatment, and counteractions to said obstructions;

processing method determining means for predicting obstructions and determining a water treatment method based on the counteractions, using rules stored in said rule base, and data concerning the detected kinds and measured quantities of plankton;

information presenting means for presenting information identifying the water treatment method determined by said processing method determining means; and a data base for storing data measured by said plankton measuring means and data concerning the water treatment method determined by said processing method determining means.

8. A system for supporting operations of a water supply plant according to claim 7, further comprising:

water quality measuring means for measuring at least one of the water quality items of pH, water temperature, water turbidity, smell, dissolved oxygen, biological oxygen demand, chemical oxygen demand, and chlorophyll density.

9. A system for supporting operations of a water supply plant according to claim 7, further comprising:

poison monitoring means for monitoring poison due to a breeding aquatic organism in water taken in from the source of intake water and detecting abnormal behaviors of the aquatic organism; and plant operation means for closing the source of intake water when detecting poison.

10. A system for supporting operations of a water supply plant having a sedimentation basin for precipitating and removing substances suspended in water taken in from a source of intake water, a filtration basin for filtering water which passes the sedimentation basin to produce filtered water, and a chlorine injection installation for disinfecting the filtered water, said system comprising:

a rule base for storing rules representing relations among different kinds of plankton and back washing intervals for the filtration basin;

plankton measuring means for detecting different kinds of plankton living in a source of intake water and measuring the quantity of each detected kind of plankton, processing method determining means for determining back washing intervals for the filtration basin by using rules stored in said rule base and input data of the detected kinds and measured quantities of plankton; and information presenting means for presenting information indicating the determined back washing intervals.

* * * * *